(12) United States Patent
Lundsgaard et al.

(10) Patent No.: US 6,413,784 B1
(45) Date of Patent: Jul. 2, 2002

(54) MULTI-SECTIONED FLUID DELIVERY DEVICES FOR DETECTING TARGET MOLECULES BY IMMUNOASSAY

(75) Inventors: Jorgen Schjerning Lundsgaard, Svendborg; David Morgan Thomas, Stenstrup; Torsten Bjoern, Soeborg, all of (DK)

(73) Assignee: Idego ApS, Albertslund (DK)

( * ) Notice: Subject to any disclaimer, the term of this patent is extended or adjusted under 35 U.S.C. 154(b) by 0 days.

(21) Appl. No.: 09/526,703

(22) Filed: Mar. 15, 2000

Related U.S. Application Data

(63) Continuation-in-part of application No. 08/985,005, filed on Dec. 4, 1997, now Pat. No. 6,048,735.

(30) Foreign Application Priority Data

Dec. 5, 1996 (DK) .............................................. 1394/96

(51) Int. Cl.[7] .......................................... G01N 33/543
(52) U.S. Cl. .................... 436/518; 422/55; 422/56; 422/57; 422/58; 422/101; 422/102; 435/287.1; 435/287.2; 435/287.7; 435/287.9; 435/288.4; 435/288.5; 435/288.7; 436/164; 436/514; 436/805; 436/807; 436/810; 604/82; 604/87; 604/89; 604/90; 604/91; 604/187; 604/190; 604/191; 604/218
(58) Field of Search ................... 604/82, 87, 89–91, 604/187, 190, 191, 218; 422/55–58, 82.05, 82.08, 82.11, 101, 102; 435/287.1, 287.2, 287.7, 287.9, 288.5, 288.4, 288.7; 436/164, 172, 518, 514, 805, 807, 810

(56) References Cited

U.S. PATENT DOCUMENTS

| | | | | |
|---|---|---|---|---|
| 4,643,721 A | * | 2/1987 | Brunet | 604/191 |
| 4,775,637 A | | 10/1988 | Sutherland | 436/427 |
| 4,792,329 A | | 12/1988 | Schreuder | 604/90 |
| 4,846,548 A | | 7/1989 | Klainer | 350/96.29 |
| 5,030,555 A | * | 7/1991 | Clemmons | 435/5 |
| 5,041,088 A | * | 8/1991 | Ritson et al. | 604/88 |
| 5,418,136 A | | 5/1995 | Miller | 435/5 |
| 5,476,449 A | * | 12/1995 | Richmond | 604/87 |
| 5,772,665 A | * | 6/1998 | Glad et al. | 604/82 |
| 6,331,173 B1 | * | 12/2001 | Ljungquist | 604/191 |

* cited by examiner

Primary Examiner—Christopher L. Chin
(74) Attorney, Agent, or Firm—Licata & Tyrrell P.C.

(57) ABSTRACT

Multi-sectioned fluid delivery devices with sensor membranes for use in detection of target molecules in gas or liquid samples are provided.

6 Claims, 6 Drawing Sheets

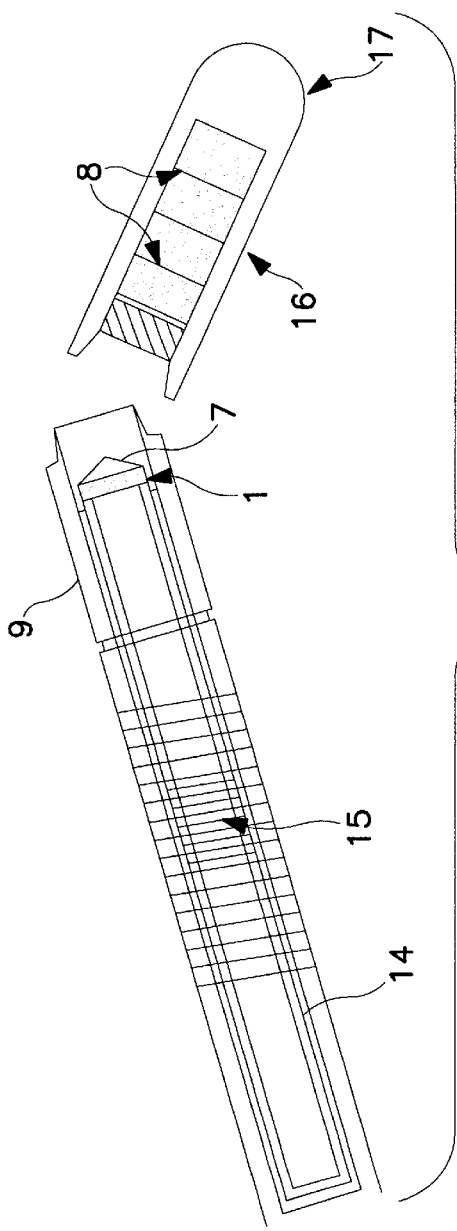
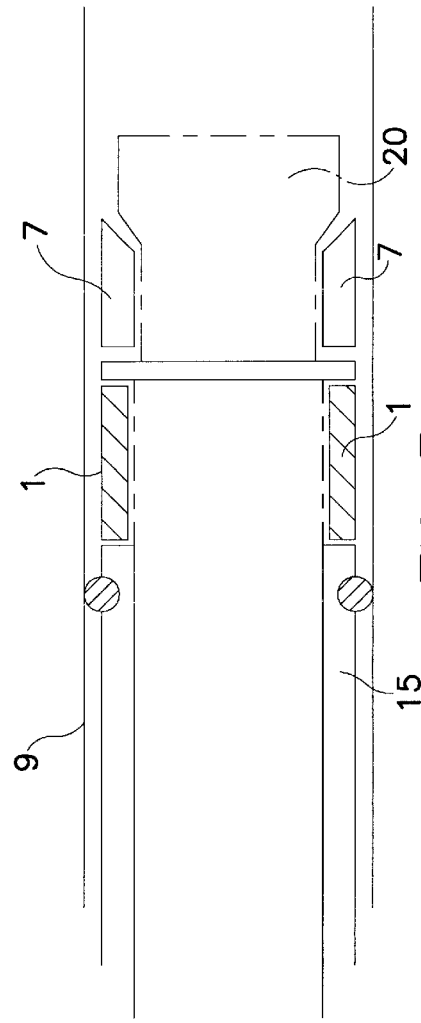
FIG. 2
FIG. 3

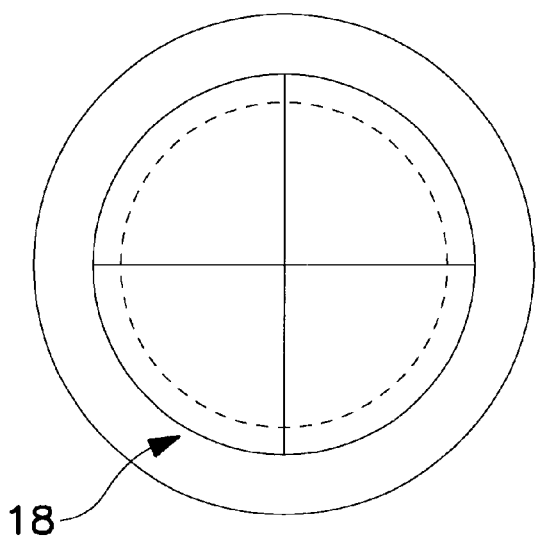
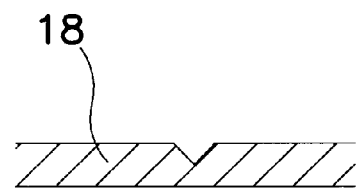
FIG. 5
FIG. 4
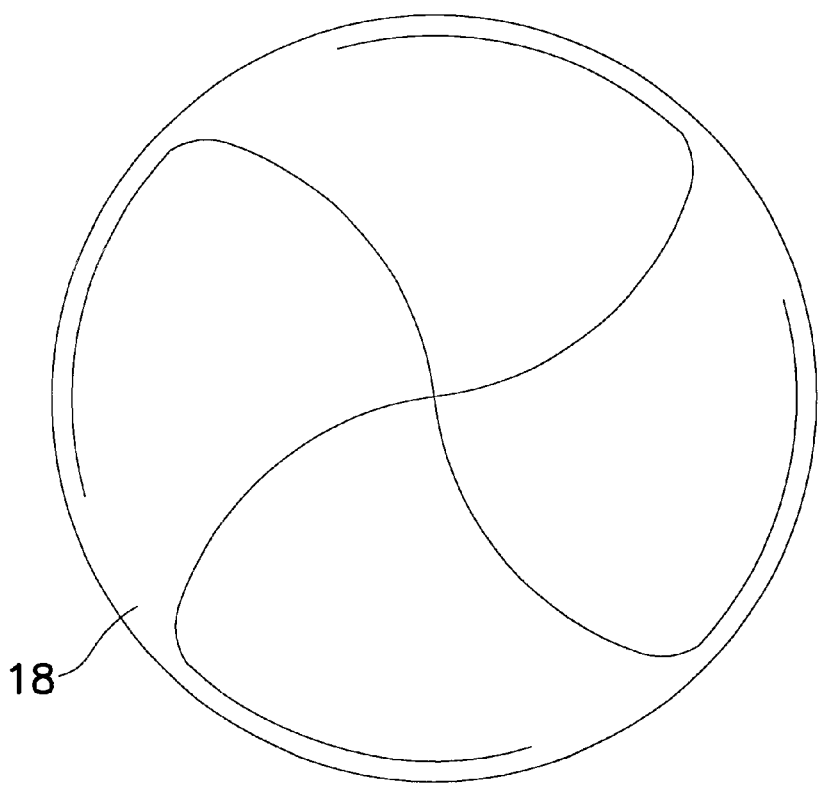
FIG. 6

MULTI-SECTIONED FLUID DELIVERY DEVICES FOR DETECTING TARGET MOLECULES BY IMMUNOASSAY

INTRODUCTION

This application is a continuation-in-part of U.S. application Ser. No. 08/985,005, filed Dec. 4, 1997, now U.S. Pat. No. 6,048,735 which is a continuation-in-part of Danish Provisional Application No. DK1394/96 filed on Dec. 5, 1996.

FIELD OF THE INVENTION

The present invention relates to multi-sectioned fluid delivery devices with sensor membranes which can be used in the detection of target molecules in gas and liquid samples.

BACKGROUND OF THE INVENTION

The detection of substances in various fluids by immunoassay methods is well known and used frequently for a variety of different purposes. Examples include the detection of antibodies in blood, urine, saliva or other biological fluids as an indication of the presence of a pathogen for diagnosis of various diseases and conditions. Other immunoassays of biological fluids include pregnancy tests and tests to determine blood alcohol level. More recently, immunoassays have been developed for detection of pollutants in environmental samples such as water and discharge from smoke stacks.

While such tests can be carried out as liquid assays, it is often easier and more convenient to spot the sample onto a solid substrate on which a ligand for the target molecule is immobilized and detect the presence of a specific binding complex. The most widespread immunoassay solid phase format used today is the enzyme-linked immunosorbent assay (ELISA).

An ELISA apparatus typically comprises a 96 well microtiter plate, the inside surfaces of which are coated with a ligand specific for a target molecule present in a sample. This binding or attachment of the ligand to the solid phase is not a chemical reaction but rather is believed to result from a physical or noncovalent interaction between the polystyrene matrix of the microtiter plate and the antigen. A sample suspected of containing the target molecule is placed in contact with the microtiter plate so that binding will occur between the ligand and any target molecule in the sample. Any unbound target molecules are then removed from the plate wells by several washing steps. A second ligand which specifically recognizes the target molecule and is linked to a signal-generating enzyme is then added. Detection of the enzyme which is indicative of the presence of the target molecule in the sample is typically performed by addition of reagents which produce a color change.

Performance of an ELISA can be quite time consuming. For example, an established method for screening for the AIDS virus is to first carry out an ELISA, followed by confirmation of positives by Western Blot. Generally, the ELISA takes about 4 hours and the Western Blot, which includes an overnight incubation period, requires about 20 hours. While this method may be adequate for routine screening of blood samples, it is not adequate for screening in organ transplant situations wherein results are required prior to the maximum ischemic time for the organ.

A similar technology, referred to as enzyme-linked immunofiltration assay (ELIFA), has been developed more recently in an attempt to overcome problems with false positive results and low sensitivity associated with ELISAs. ELIFAs function very similarly to ELISAs with the exception that ELIFA takes advantage of filtering the initial solution containing the ligand through a nitrocellulose membrane to bind it to the membrane. This filtering process facilitates "immunoconcentration" in that much higher levels of ligand bind to the membrane as compared to levels of ligand that bind to the surface of a microtiter plate. Target molecules in a sample are then bound to the ligand by incubation as in the ELISA method. However, any unbound target molecule is removed from the membrane by filtration of the unbound molecules through the membrane into a waste chamber. Bound molecule is detected by precipitating a colored product on the membrane.

This type of porous solid substrate is, in theory, very useful since it permits removal of the bulk of the sample from the substrate while the target molecule remains at the surface bound to the immobilized ligand. However, in practice there are considerable difficulties due to slow flow of the sample through the substrate thus making this type of assay also very time consuming.

The present invention relates to a multi-sectioned fluid delivery device which is used in the ordered delivery of various fluids to a sensor membrane for detection of a targeted molecule bound to the sensor membrane.

A multi-compartment syringe is disclosed by Schreuder in U.S. Pat. No. 4,792,329. This syringe comprises an ampule having a plunger, a sealing stopper and at least one separating stopper between the plunger and the sealing stopper, and a needle holder consisting of a collar, a neck for an injection needle, a shaft between the collar and the neck and a by-pass means in the inner wall of the shaft, the space in the shaft of the needle holder being at least slightly longer that the sealing stopper, the ampule wall comprising a liquid by-pass means through which the liquid behind the separating stopper or stoppers can reach the substance in front of the separating stopper or front separating stopper and can mix with the same or can dissolve it, the ampule, before use of the syringe comprising an empty space in front of the sealing stopper. Thus, this device is different both functionally and in design from the multi-sectioned fluid delivery device of the present invention.

SUMMARY OF THE INVENTION

An object of the invention is to provide a multi-sectioned fluid delivery device which can be used for the ordered delivery of various fluids to a sensor membrane integrally linked or located within the multi-sectioned fluid delivery device. The delivery device of the present invention comprises a hollow syringe, and a piercing element and multiple individual compartments for separate storage of controlled amounts of various fluids located within the hollow syringe. Fluids are released from their individual compartments in the hollow syringe onto a sensor membrane in a prescribed sequence upon piercing of each compartment.

Another object of the present invention is to provide methods of using the multi-sectioned fluid delivery device in the detection of selected target molecules in a gas or liquid sample via a sensor membrane.

BRIEF DESCRIPTION OF THE DRAWINGS

FIG. 2 provides a schematic representation of a second embodiment of a multi-sectioned fluid delivery device.

FIG. 3 provides a schematic representation of a preferred embodiment of a plunger, sensor membrane and piercing element which can be used in the multi-sectioned fluid delivery device depicted in FIG. 2.

FIG. 4 provides a top view of one embodiment of a divider which separates the multiple compartments of the multi-sectioned fluid delivery device depicted in FIG. 2.

FIG. 5 provides a cross section al view of the divider depicted in FIG. 4.

FIG. 6 provides a top view of a preferred embodiment of a divider which separates the multiple compartments of the multi-sectioned fluid delivery device depicted in FIG. 2.

FIG. 7(a) shows the collection unit removed from the multi-sectioned fluid delivery device. FIG. 7(b) shows the collection unit after collection of the sample as it is inserted back into the multi-sectioned fluid delivery device. FIG. 7(c) shows the collection unit as the collected sample is transferred to a compartment of the multi-sectioned fluid delivery device.

FIG. 8(a) shows the collection unit removed from multi-sectioned fluid delivery device. FIG. 8(b) shows the collection unit inserted in the multi-sectioned fluid delivery device following immersion in the sample fluid. FIG. 8(c) shows the collection unit as the sample is transferred into the compartment of the multi-sectioned fluid delivery device.

DETAILED DESCRIPTION OF THE INVENTION

Figure 1:
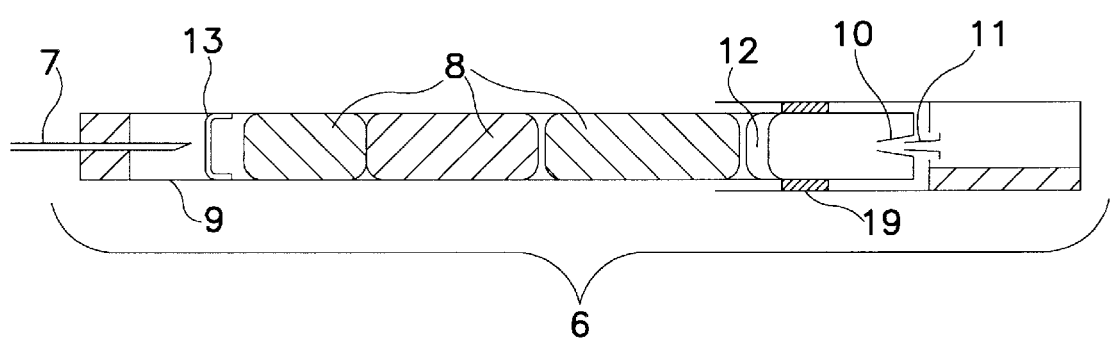
FIG. 1 provides a schematic representation of a first embodiment of a multi-sectioned fluid delivery device.

The present invention relates to multi-sectioned fluid delivery devices, preferred embodiments of which are depicted in FIGS. 1 through 3, which can be used to deliver controlled amounts of fluids in a prescribed sequence to a sensor membrane. In a preferred embodiment, the fluids in the syringe are those fluids routinely used by those of skill in the art in ELISAs which are also required to detect target molecule bound to a sensor membrane. Examples of fluids which may be incorporated into the multi-sectioned fluid delivery device include, but are not limited to, a fluid comprising a labeled second ligand for the target molecule, a fluid containing a means for detecting the label of the second ligand, and wash buffers.

In simplest form, the multi-sectioned fluid delivery device comprises a hollow syringe having an interior and exterior and a proximal and distal end. The hollow syringe is open at the distal end for insertion of a piercing component into the interior of the hollow syringe. Located in the interior of the hollow syringe between the proximal end and the piercing element are multiple individual compartments for separate storage of controlled amounts of various fluids. Fluids are released from their compartments in a prescribed sequence upon piercing of each individual compartment in the hollow syringe by the piercing element. A sensor membrane is integrally linked to or located within the hollow syringe of the multi-sectioned fluid delivery device so that the sensor membrane is exposed to the sequentially released fluids.

Various configurations of these elements in the present invention are depicted in FIGS. 1–3.

In one embodiment, as depicted in FIG. 1, the multi-sectioned fluid delivery device 6 comprises a hollow syringe 9 having a distal and proximal end. The proximal end of the syringe 9 is sealed. The distal end of syringe is open and contains a fixing means 19, preferably threads, to which is attached a nozzle 10 and valve 11 for controlled delivery of a liquid or gas to the interior of the hollow syringe 9. A first slidable piston 12 is located in the interior of the syringe 9 at the distal end. A second slidable piston having a weakened center 13 is located in the interior of the hollow syringe 9 near the proximal end. The weakened center of the second slidable piston 13 permits piercing of the piston 13 by a piercing component 7 upon movement of the second piston 13 toward the piercing element 7. Multiple compartments 8, in this embodiment polymer bags, each containing a fixed amount or volume of fluid, are located between the first 12 and second 13 slidable pistons. A piercing element 7, preferably an injection needle in this embodiment, is inserted into the hollow syringe 9 through the sealed proximal end so that upon entry of a gas or liquid through the nozzle 10 and valve 11 into the interior of the hollow syringe 9, resulting pressure in the interior of the syringe 9 slides the first 12 and second 13 pistons and multiple compartments 8 containing each fluid toward the proximal end of the hollow syringe 9 and the piercing element 7. Regulation of the flow and pressure of the gas or liquid in the interior of the syringe 9 permits controlled sequential release of each liquid by pushing the second piston having a weakened center 13 over the piercing element 7 so that a first compartment 8 closest to the proximal end of the syringe 9 is pierced by the piercing element 7 and fluid from this compartment is released. Continued pressure results in piercing and release of a fluid in the next compartment 8 and so forth until all fluids required for reaction have been released. In a preferred embodiment, fluids from the fluid delivery device 6 flow out of the syringe 9 via the injection needle 7 into a tube having attached at the other end a sensor membrane 1 which has been exposed to the biological sample. In this embodiment, the sensor membrane 1 further comprises a treatment dock designed for insertion of the sensor membrane after exposure to the biological sample into one end of the tube. Thereafter, insertion of the multi-sectioned fluid delivery device at the other end of the tube provides a route for treatment liquids ejected from the syringe. The fluids pass through the sensor membrane in a well defined manner and in proper sequence and duration in a controlled environment.

In another embodiment, as depicted in FIG. 2, the multi-sectioned fluid delivery device 6 comprises a hollow syringe 9 having a distal and proximal end with a removable cap 16 containing multiple compartments 8 for separate storage of liquids at the distal end of the hollow syringe 9. A turning handle 14 is located at the proximal end of the syringe 9 which is integrally linked to a plunger 15 inside the hollow syringe 9, said plunger also having a distal and proximal end. The plunger 15 continues from the proximal end of the interior of the hollow syringe 9 wherein it is linked at its proximal end to the turning handle 14 toward the distal end of the syringe 9. The plunger is attached at its distal end to a sensor membrane 1 and a piercing element 7. As shown in FIG. 2, the sensor membrane 1 may be positioned between the distal end of the plunger 15 and the piercing element 7. Alternatively, as depicted in FIG. 3, one or more sensor membranes 1 may be positioned on each side of the distal end of the plunger 15 running parallel to the interior of the hollow syringe 9. In this preferred embodiment, an absorber 20 is attached at the distal end of the plunger between two piercing elements 7 to assist in opening of each compartment following piercing to insure that the complete volume of fluid in each individual compartment is released. In this embodiment, each multiple compartment 8 of the fitted cap 16 is separated by dividers 18, preferably dividers such as those depicted in FIGS. 4, 5 or 6, so that fluids required for detection of a target molecule in a biological sample may be stored separately in individual compartments of the fitted cap 16. As shown in FIGS. 4 through 6, the surface of the divider is molded or etched with stress raisers which reduce the thickness of the cross section of the divider in selected areas so that upon piercing the divider tears along the stress raisers in a preferred manner thereby releasing all of the fluid in the individual compartment. In a preferred embodiment, as depicted in FIG. 6, the stress raisers are S-shaped. It is also preferred that the cap 16 further comprise a magnified or spectrophotometric reading area 17 for easy detection of any target molecule bound to the sensor membrane. Spectrophotometric reading areas which can be adapted for use in the present invention have been described in U.S. Pat. No. 4,775,637. In this embodiment, the fitted cap 16 is removed from the distal end of the syringe 9 and a biological sample is placed in the cap. The cap 16 is then fitted onto the distal end of the syringe 9 so that the biological sample comes into contact with the sensor membrane 1 and permits binding of any target molecule in the sample to a sensor membrane 1. The turning handle 14 is then rotated so that the plunger 15, sensor membrane 1 and piercing element 7 move toward the distal end of the syringe 9 extending into the cap 16 so that the piercing element 7 sequentially pierces each divider 18 of each compartment 8 thereby releasing the fluids in an ordered sequence to detect any bound target molecule on the sensor membrane 1.

Figure 7A:
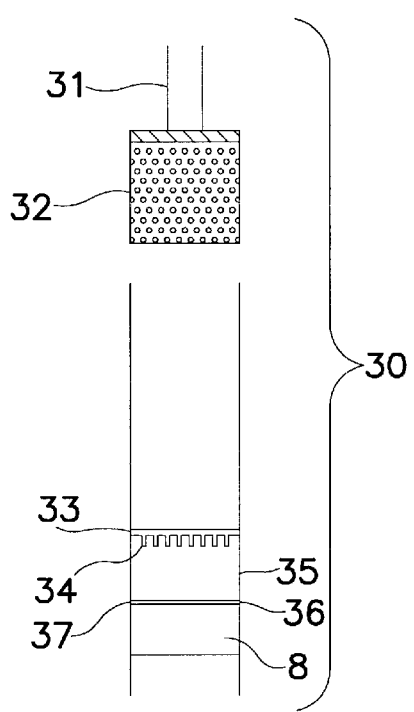
FIGS. 7a–7c provide a diagram of a collection unit in three transfer stages with sample pre-treatment.
Figure 7B:
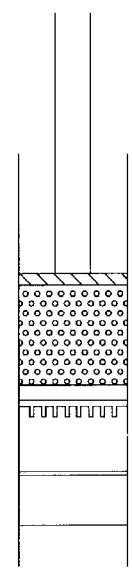
Figure 7C:
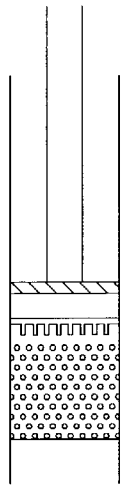

Preferably, the multi-sectioned fluid delivery devices of the present invention further comprise a sampler or collection unit 30 for use in transferring a biological fluid such as saliva to an individual compartment of the multi-sectioned fluid delivery device. Techniques are available for transferring the sample to a compartment directly prior to the sensor membrane or to a vacant compartment in the second compartment position so that a pre-flush of the sensor membrane can be carried out. FIGS. 7(a), 7(b) and 7(c) shows a collection unit for use in transfer of a biological fluid to a compartment of the multi-sectioned fluid delivery device directly prior to the sensor membrane. In this embodiment, the biological fluid can be filtered or chemically conditioned by exposure to selected agents during the transfer process. Sample collection and transfer of the biological fluid to the multi-sectioned fluid delivery device comprises 3 stages. In stage 1, as depicted in FIG. 7(a), the collection unit piston 31 with the affixed absorbent 32 is removed from the multi-sectioned fluid delivery device. In stage 2, the absorbent 32 is immersed in the biological fluid. As depicted in FIG. 7(b), the wetted absorbent 32 is then placed back in the collection unit 30 and the piston 31 is then moved in order to compress the absorbent 32, thus expelling the fluid sample through the filter 33, which is mechanically supported by a supporting mesh 34, into the conditioning compartment 35. During this process the fluid is homogenized by the flow through the filter 33 and solid contaminants, gel and other unwanted materials are removed. Liquid entry into the conditioning compartment 35 creates a rise in pressure which is compensated by exhaust of gas, i.e. air or a protective gas, through relieving vents 37. On further movement of the piston 31 past the relieving vents 37, as depicted in FIG. 7(c), pressure rises on a separator membrane 36 which is sufficient to penetrate the membrane so that the treated sample is transferred to a compartment 8 of the multi-sectioned fluid delivery device.

Figures 8A, 8B, 8C:
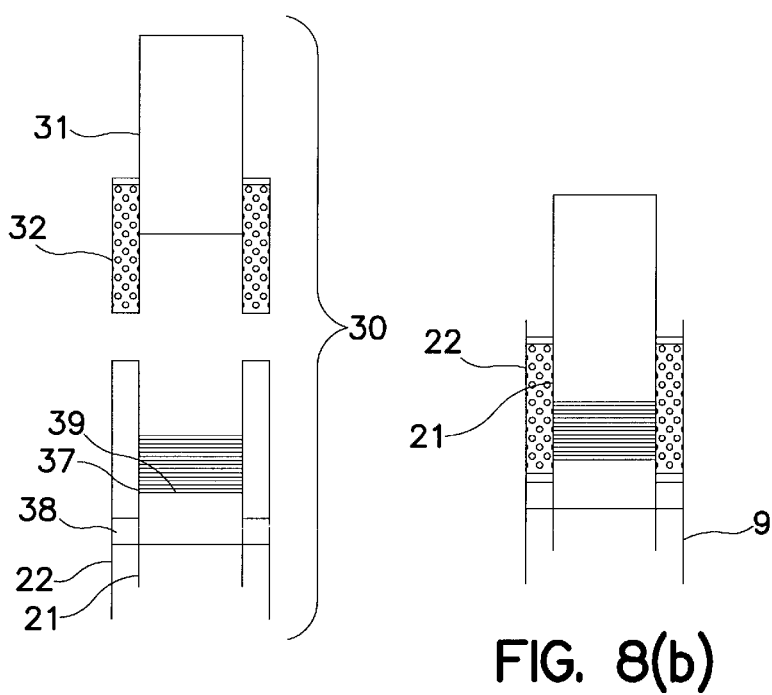
FIGS. 8a–8c provide a diagram of a collection unit in three transfer stages with sample conditioning of the sensor membrane before contact with the biological fluid. In this embodiment, the biological fluid is against transferred to a compartment of the multi-sectioned fluid delivery device.
Figure 9:
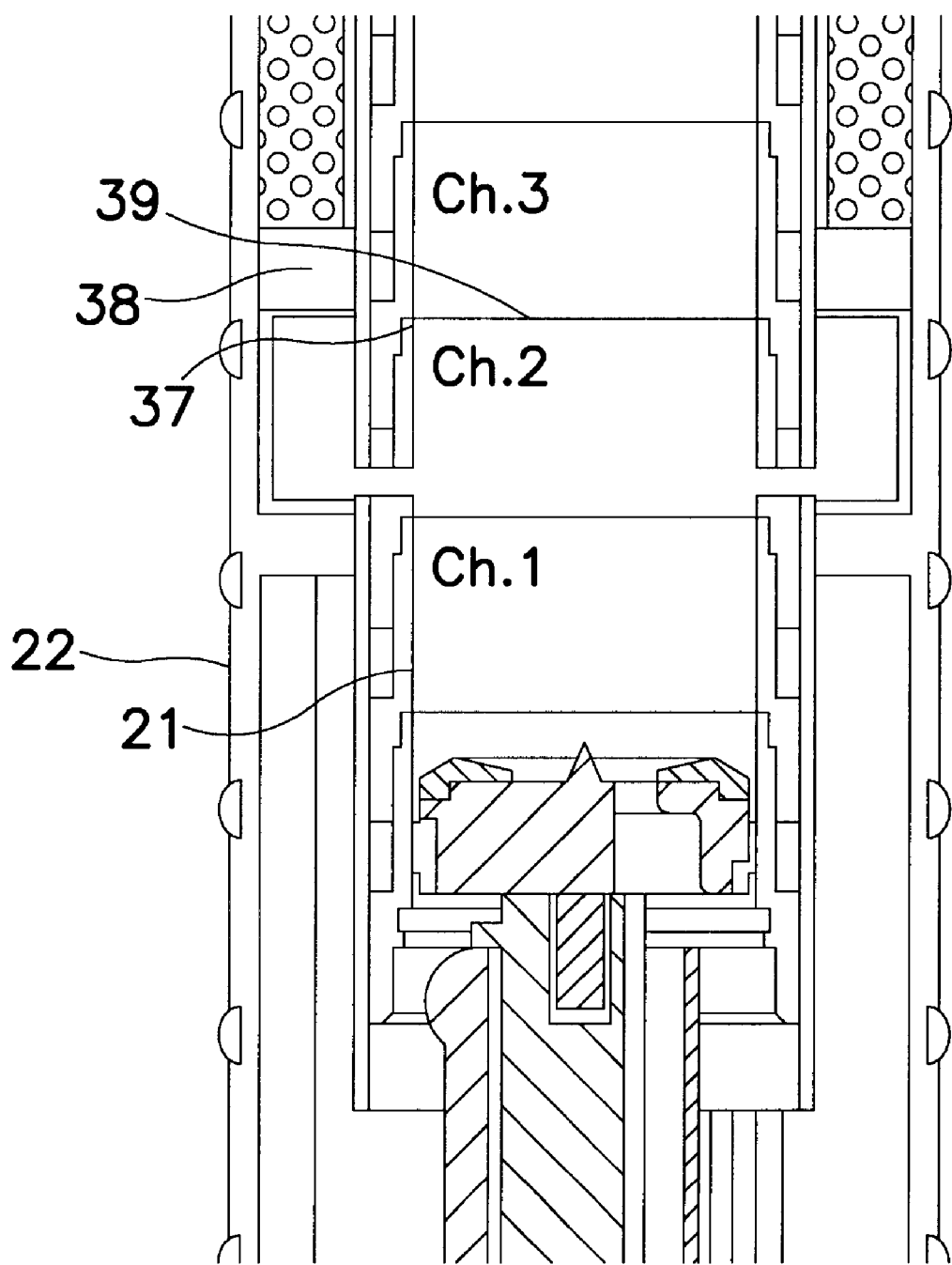
FIG. 9 is a diagram of a preferred embodiment of the collection unit of FIG. 8, wherein the sample is transferred to a second compartment to allow for a pre-wash step of the sensor membrane by including a pre-wash fluid in the first compartment.

FIGS. 8(a), 8(b) and 8(c) shows another embodiment of a collection unit. Also see FIG. 9 which provides a preferred embodiment of this collection unit wherein the sample is transferred to a vacant compartment in the second individual compartment position (Ch. 2) so that a pre-flush for the sensor membrane can be incorporated into the first individual compartment (Ch. 1). The transfer process in either embodiment comprises three stages. In stage 1, as depicted in 8(a), the collection unit piston 31 with the affixed absorbent 32 is removed from the multi-sectioned fluid delivery device and the absorbent 32 is immersed into the sample fluid. In stage 2, as depicted in FIG. 8(b), the absorbent 32 is inserted and docked into the annular orifice between the outer 22 and inner wall 21 of the hollow syringe 9 of the multi-sectioned fluid delivery device. As shown in FIG. 8(c) upon compression of the absorbent, the sample fluid is ejected and is forced through a porous annular ring 38 through apertures 39 into its final receptacle which is the second compartment 8 of a multi-sectioned fluid delivery device. For saliva samples it is preferred that the porous annular ring 38 contain a conditioning chemical treatment for decreasing viscosity of the saliva samples. Relieving vents 37 are provided to compensate for pressure and allow for exhaust of trapped gases.

As will be obvious to those of skill in the art other configurations and/or arrangements of these elements not specifically set forth herein which result in sequential release of fluids upon piercing of individual compartments in the hollow syringe are considered to be within the scope of this invention.

Various sensor membranes capable of binding a target molecule are useful in the present invention. For example, an unsupported nitrocellulose membrane coated with a ligand for the target molecule can be used. It is preferred that the membrane have a defined pore size to allow free passage of non-captured microspheres. Free passage is achieved when the pore size is at least ten times larger that the microspheres. It is also preferred that membrane be of sufficient thickness to be adequately rigid to sustain the fluid pressure as the membrane mounted on the plunger is moved forward. For example, a membrane with a diameter of 0.5 mm, and thickness of 1 $\mu$m and a pore size of at least 3 $\mu$m was demonstrated to be useful for a total fluid volume of 20 milliliters over an 8 minutes assay period. Various nitrocellulose membranes meeting these requirements are available commercially from vendors including, but not limited to, Whatman, Micro Filtration System Inc., Schleicher and Schuell, and Sartorius AG.

Sensor membranes useful in the present invention may also comprise parallel fibers configured as a bundle or piece of rope. Bundles of fibers provide a considerable exterior surface to which ligands and targeted molecules can be attached. Upon binding of a target molecule to the fiber, the fiber is optically changed. More specifically, it is well known from fiber optics that light refraction occurs just outside the fiber surface which the phase changes. Light emerging after transmission through this fiber is changed thus becoming amenable to quantifying measurements on spectral modification and intensity. Sensor membranes which detect the presence of an analyte based upon light interference and which may be adapted for use in the devices of the present invention have been described in U.S. Pat. No. 5,418,136, U.S. Pat. No. 4,486,548 and U.S. Pat. No. 4,846,548.

The sensor membrane of the multi-sectioned fluid delivery device may also comprise a sensor laminate. Sensor laminates useful in this device preferably comprise a polymer base; a reactive substrate layer superimposed on the polymer base; and a saliva activation layer superimposed on the reactive substrate layer. The polymer base is comprised of a suitable nonporous polymer such as polystyrene, polysiloxane, polystyrene-butadiene co-polymers, polyethylene, polypropylene, ethylene vinyl acetate, polyvinylchloride, tetrafluoroethylene, polycarbonate or polysulfone which have a fiber size which renders them nonporous. The reactive substrate layer is comprised of a selected ligand for the target molecule interspersed widely throughout the layer and bound to a polymeric material treated to enhance binding of the ligand to the polymeric material. Examples of polymeric materials which can be used in the reactive substrate layer also include, but are not limited to, polystyrene, polysiloxane, polystyrene-butadiene co-polymers, polyethylene, polypropylene, ethylene vinyl acetate, polyvinylchloride, tetrafluoroethylene, polycarbonate and polysulfone. The top saliva activation layer is comprised of a soluble material such as 3% citric acid in polyvinyl pyrrolidone which promotes the production of ample quantities of saliva and permits diffusion of target molecules in the saliva sample placed upon this layer into the reactive substrate layer beneath. This sensor laminate can be placed directly in the mouth so that a saliva sample collects on the top saliva activation layer. The sample diffuses into the reactive substrate layer wherein target molecules in the sample bind to ligand. Bound target molecules are then detected by contacting the reactive substrate layer with standard detection reagents delivered in sequence via a multi-sectioned fluid delivery device of the present invention. For example, in one embodiment the multi-sectioned fluid delivery device will deliver a detection reagent comprise a second ligand for the target molecule, said second ligand being detectably labeled. Examples of detectable labels include fluorometric agents such as fluorescein isothiocyanate or calorimetric agents such as horse radish peroxidase. Additional reagents required for detection of such labels which are well known to those of skill in the art can then be delivered subsequently via the multi-sectioned fluid delivery device, In a preferred embodiment, the sensor laminate further comprises an absorptive layer located between the polymer base and the reactive substrate layer. In this embodiment, the polymer base comprises any suitable permeable polymeric sheet which provides for good bonding to the absorptive layer. Examples include, but are not limited to, polystyrene, polysiloxane, polystyrene-butadiene co-polymers, polyethylene, polypropylene, ethylene vinyl acetate, polyvinylchloride, tetrafluoroethylene, polycarbonate and polysulfone which have a fiber size which renders them permeable. The absorptive layer bonded to the polymer base comprises a porous and permeable material such as cellulose paper with a polyacrylate salt which absorbs excess sample fluid and the various fluids used in detection of target molecules bound to the reactive substrate layer.

These sensor laminates can be manufactured by chemically bonded a selected ligand to a polymeric material to produce a reactive substrate layer. In this method, the sensor laminate is manufactured by process technology using laminating and coating techniques well known and routinely used in the electrochemical industry. However, these techniques have been modified to include the integration of a ligand into the polymeric material using chemical and radiation activated bonding processes. In one embodiment, the polymeric material is irradiated prior to contacting with the ligand. Alternatively, the polymeric material may be treated by irradiation in the presence of the ligand. In contrast to conventional surface adsorption with subsequent degradation, these processes provide for enhanced chemical bonding, including increased capacity, affinity and stability, of a ligand to the polymeric material.

In one embodiment, a sensor laminate is prepared from a suitably sized polymeric base layer stamped out from a large sheet of a polystyrene felt. The polystyrene felt is irradiated with an electron beam. The irradiated polystyrene felt is coated with ligand by incubating the polystyrene felt for approximately two hours at room temperature in a sample of ligand diluted at a suitable concentration in coating buffer such as phosphate buffered saline; 0.01 M sodium-potassium-phosphate buffer, 0.0027 M potassium chloride, 0.0137 M sodium chloride, pH 7.4; or 0.05 M carbonate-bicarbonate buffer, pH 9.6. To remove non-bound ligand, the ligand-coated polystyrene felt is washed three times with a wash buffer such as PBS+0.1% Tween 20. To block non-bound ligand binding sites, the ligand-coated polystyrene felt is incubated for two hours at room temperature with a blocking buffer such as PBS+0.5% Tween 20. The ligand-coated polystyrene-felt is then washed again to remove blocking buffer. The ligand coated polystyrene felt sample which serves as the sensor laminate is then dried.

Further, it has been found that initiation of free radicals by electron beam in a sensor membrane comprising a polymeric material enhances binding of a ligand to the polymeric material of the sensor membrane. For example, polystyrene surfaces exposed to electron beam activation demonstrated markedly increased affinity for selected ligands. Further, bonding between the electron beam-treated polystyrene sensor membrane and the selected ligand is strong. The binding of ligands to solid polymeric supports has three basic components: capacity, affinity, and stability. Capacity is the maximum amount of material that can be bound per surface area of support. Affinity is the degree of attraction between the ligand and the support. Stability is the level of permanence of the bond between the ligand and the support. Prior art methods have primarily focused upon enhancing capacity of the solid support since affinity and stability were believed to be inherent features of the particular polymeric material. By the phrase "enhanced binding" as used herein, it is meant that capacity, affinity and stability of the polymeric material for the ligand are increased. The present invention provides sensor membranes for use with the multi-sectioned fluid delivery devices for detection of selected target molecules in gas or liquid samples which comprise a sensor laminate having a reactive substrate layer wherein the reactive substrate layer comprises a ligand for a selected target molecule bound to a polymeric material which has been treated to enhance binding of the ligand to the polymeric material. Enhanced binding of the ligand of the reactive substrate layer to the polymeric base layer is achieved by treatments such as admixture or by chemical grafting. Techniques used for grafting include steps for free radical initiation, for example, by irradiation techniques including, but not limited to, electron beam treatment or sonochemical techniques.

Another means for increasing the ligand and/or target molecule bound to the sensor membrane of the present invention comprises vacuum filtration of the ligand or the gas or liquid sample containing the target molecule through the sensor membrane. Upon filtration under vacuum, any ligand or target molecule in the sample will bind to the sensor membrane. The sensor membrane can then be mounted onto the plunger of the multi-sectioned fluid delivery device for the immunoassay.

The present invention also provides methods of using the multi-sectioned fluid delivery devices in the detection of target molecules in gas or liquid samples. A multitude of recent studies have shown direct correlation of blood and saliva as test matrixes for disease detection. Gingival crevicular fluid is a serum transudate present in the mouth which closely resembles serum. This saliva transudate exhibits blood concentrates of HIV antibodies comparable to blood concentrates to give accurate test using a specially adjusted enzyme linked immunosorbent assay (ELISA). Recent studies have shown *Helicobacter pylori*, a well known causative factor in the development of both duodenal and gastric ulcers, to have a similar presence of antigens/antibodies in saliva. The multi-sectioned fluid delivery devices are particularly useful in assays which detect target molecules in saliva.

For example, devices of the present invention can be used in the detection of target molecules such as *H. pylori* antibodies in saliva samples. In this method the sensor membrane is wetted with a fluid such as PBS-buffer in a first compartment of the multi-sectioned fluid delivery device. The biological sample, i.e., saliva, is then added to the sensor membrane so that any target molecule, i.e. *H. pylori* antibodies, in the sample can bind to the sensor membrane. In one embodiment of the device which comprises a collection unit, the externally acquired biological fluid is transferred to an individual compartment of the device. As depicted in FIGS. 7 and 8, techniques are available for transferring the sample to compartments directly prior to a sensor membrane positioned on the advancing piston head, or to a vacant compartment in the second position so that a pre-flush of the sensor membrane can be carried out by penetrating the first compartment prior to exposing the sensor membrane to the sample by penetrating the second compartment. The sensor membrane is then washed with a wash buffer released from the second or third compartment of the multi-sectioned fluid delivery device so that nonbound components of the sample are washed through or from the sensor membrane. Following this wash step, the sensor membrane is contacted with a solution from the next compartment comprising antibody coated dyed latex particles which recognize and bind to target molecule bound to the sensor membrane. The sensor membrane is then washed again with wash buffer in the following compartment to remove any nonbound latex particles. Target molecule is detected by the appearance of color resulting from the bound latex particles on the sensor laminate.

The following nonlimiting examples are provided to further illustrate the present invention.

EXAMPLES

Example 1

Manufacture of Polystyrene Fibers for use in Sensor Membranes

Polystyrene is melted by heating to 190–200° C. A thread is selected from the melt surface and drawn to a diameter of 30 to 50 $\mu$M. The fibers are cut to a nominal 2–3 mm in length.

Example 2

Manufacture of Sensor Membranes Comprising a Polystyrene Filter

Experimentally, 25 cm$^2$ of the polystyrene filter has been manufactured at a time. This uses 0.5 grams of polystyrene cut fiber with a length of 2–3 mm corresponding to a weight of 0.2 kg/m$^2$. The fibers are spread on an inactive surface so that they are separated from each other. The fibers are then collected in the area required. A solvent mix consisting of 45% ethanol and 55% 2-butadone (methyl ethyl ketone) is added corresponding to 0.6 L/m$^2$. The fibers are then roller compressed by a cylinder with a pressure of 1 kg/linear cm. The roller passes over the fibers 5 times in all. It is important to avoid adhesion to the inactive substrate and the roller. Excess solvent is removed immediately by suction and the filter is dried in a hot air current.

The polystyrene filter is washed in ethanol and dried. The filter is then electron beam treated using an area beam type electron beam processing system referred to as CURETRON (Type EBC-200-AAS, Nissin-HighVoltage, Co. Ltd., Kyoto, 615, Japan) under the following conditions:

Voltage: 190 kV

Current: 4 mA

Conveyor speed: 4 m/minute

Atmosphere: 6 Nm$^3$/minute nitrogen.

Example 3

Test System with Streptavidin Coupled Latex and Biotinylated Tetanus Toxoid For these assays, nitrocellulose membranes (pore size=5 $\mu$m) sheet (diameter 7 mm) were coated with tetanus toxoid (TT; 2.23 mg/ml) or biotinylated tetanus toxoid (TT$^B$; 0.9 mg/ml) at a final concentration of 200 $\mu$g/ml by incubation overnight at 4° C in high humidity. Sheets were then washed in a reservoir with Tween buffer (PBS with 1% BSA and 3% Tween 20) to remove excess TT or TT$^B$. In order to avoid further protein binding to the nitrocellulose sheets, they were then submerged into another reservoir of Tween buffer and incubated for 4 hours at room temperature. After this blocking step, the membrane was mounted on the plunger of the multi-sectioned fluid delivery device. Dark blue colored streptavidin coupled latex microspheres (Bangs Lab., Fishers, Ind.) were used for visualization. The binding reaction occurred as the solution slowly passed the membrane. Flow rate was controlled by varying the speed of the plunger and the amount of streptavidin. Captured microspheres were measured visually and were observed only on the membrane coated with TT$^B$. These experiments demonstrated functionality of the multi-sectioned fluid delivery device in an assay with a total reaction time of less than 9 minutes.

Functionality of the device of the present invention was also demonstrated in similar experiments wherein the first compartment of the multi-sectioned fluid delivery device was filled with rabbit serum with anti-TT immunoglobulins. This compartment was pierced so that its contents were in contact with the sensor membrane coated with tetanus toxoid. Biotinylated monoclonal mouse anti-rabbit IgG and streptavidin coated latex particles were then used to visualize target molecule bound to the sensor membrane.

What is claimed is:

1. A multi-sectioned fluid delivery device for sequential delivery of multiple fluids comprising:

a hollow syringe having an interior and exterior and a proximal and distal end;

a piercing element located on the interior of the hollow syringe at the proximal end;

multiple individual compartments for separate storage of various fluids located on the interior of the hollow syringe adjacent to the piercing element and extending toward the distal end of the hollow syringe; and a sensor membrane integrally linked or located within the hollow syringe so that the sensor membrane is exposed to fluids sequentially released from the multiple individual compartments.

2. The multi-sectioned fluid delivery device of claim 1 further comprising:

a fixing means at the distal end of the hollow syringe;

a nozzle and valve for controlled delivery of a liquid or gas to the interior of the hollow syringe which fixes to the distal end of the hollow syringe;

a first slidable piston located in the interior of the hollow syringe distal to the multiple individual compartments; and a second slidable piston capable of being pierced which is located in the interior of the hollow syringe at the proximal end between the piercing element and the multiple individual compartments;

so that upon entry of a gas or liquid through the nozzle and valve into the interior of the syringe resulting pressure in the interior of the hollow syringe slides the first and second pistons and the multiple compartments containing each liquid toward the proximal end of the syringe and the piercing element.

3. The multi-sectioned fluid delivery device of claim 1 wherein said hollow syringe contains a removable cap portion at the distal end and said multiple individual compartments for separate storage of various fluids are located in the removable cap of the hollow syringe.

4. The multi-sectioned fluid delivery device of claim 3 further comprising:

a turning handle located at the proximal end of the hollow syringe; and a plunger which extends from the proximal end of the interior of the hollow syringe toward the distal end of the interior of the hollow syringe, said plunger having a distal end and a proximal end which is integrally linked to the turning handle;

wherein the sensor membrane and the piercing element are attached to the distal end of the plunger so that upon rotation of the turning handle the plunger, sensor laminate and piercing element move toward the distal end of the hollow syringe extending into the cap and eventually sequentially piercing each compartment thereby releasing the fluids in an ordered sequence onto the sensor membrane.

5. The multi-sectioned fluid delivery device of claim 1 further comprising a collection unit for transferring a sample to an individual compartment in the hollow syringe of the multi-sectioned fluid delivery device.

6. A method of detecting a selected target molecule in a sample comprising contacting the sensor membrane of the multi-sectioned fluid delivery device of claim 1 with a sample so that any targeted molecules in the sample bind to the sensor membrane and sequentially exposing the sensor membrane to fluids in the multiple individual compartments of the hollow syringe of the multi-sectioned fluid delivery device so that any targeted molecule bound to the sensor membrane is detected.

* * * * *